(12) United States Patent
Kawarai et al.

(10) Patent No.: US 10,858,621 B2
(45) Date of Patent: Dec. 8, 2020

(54) CELL DISPERSION MEASUREMENT MECHANISM, AND CELL SUBCULTURE SYSTEM UTILIZING SAME

(71) Applicant: Hitachi High-Tech Corporation, Tokyo (JP)

(72) Inventors: Masako Kawarai, Tokyo (JP); Akihiro Shimase, Tokyo (JP); Sadamitsu Aso, Tokyo (JP); Toshinari Sakurai, Tokyo (JP); Eiichiro Takada, Tokyo (JP); Kazumichi Imai, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 521 days.

(21) Appl. No.: 15/320,369

(22) PCT Filed: Jul. 8, 2015

(86) PCT No.: PCT/JP2015/069617
§ 371 (c)(1),
(2) Date: Dec. 20, 2016

(87) PCT Pub. No.: WO2016/013395
PCT Pub. Date: Jan. 28, 2016

(65) Prior Publication Data
US 2017/0191019 A1    Jul. 6, 2017

(30) Foreign Application Priority Data

Jul. 22, 2014 (JP) .................................. 2014-148768

(51) Int. Cl.
*C12M 1/00* (2006.01)
*C12M 1/26* (2006.01)
(Continued)

(52) U.S. Cl.
CPC ............ *C12M 33/00* (2013.01); *C12M 29/00* (2013.01); *C12M 41/00* (2013.01); *C12M 41/36* (2013.01);
(Continued)

(58) Field of Classification Search
CPC ...................................................... G01N 1/00
See application file for complete search history.

(56) References Cited

U.S. PATENT DOCUMENTS 5,365,559 A * 11/1994 Hsueh ................ G01N 15/0205
324/71.4
2003/0054335 A1    3/2003 Taya et al.
(Continued)

FOREIGN PATENT DOCUMENTS

JP    2006-239538 A    9/2006
JP    2007-143524 A    6/2007
(Continued)

OTHER PUBLICATIONS

International Search Report (PCT/ISA/210) issued in PCT Application No. PCT/JP2015/069617 dated Oct. 13, 2015 with English translation (Four (4) pages).
(Continued)

*Primary Examiner* — Jyoti Nagpaul
(74) *Attorney, Agent, or Firm* — Crowell & Moring LLP

(57) ABSTRACT

The present invention addresses the problem of providing: a cell dispersion measurement mechanism whereby it becomes possible to fully disperse cells regardless of the experiences of operators skilled in cell culture and it also becomes possible to determine the number or concentration of cells accurately; a cell culture apparatus equipped with the cell dispersion measurement mechanism; and a cell dispersion measurement method. The problem can be solved by circulating a cell suspension in a flow path to disperse cell (Continued)

masses contained in the cell suspension, and then determining over time the number or concentration of cells and/or the degree of dispersion of cells in the cell suspension that is flowing in the circulation flow path.

14 Claims, 6 Drawing Sheets

(51) Int. Cl.
  *G01N 21/53*    (2006.01)
  *G01N 21/51*    (2006.01)
  *C12M 1/34*    (2006.01)
  *C12Q 1/02*    (2006.01)
  *C12M 1/36*    (2006.01)
  *G01N 15/06*    (2006.01)
  *G01N 21/47*    (2006.01)
  *G01N 21/59*    (2006.01)
  *G01N 15/00*    (2006.01)

(52) U.S. Cl.
  CPC ............... *C12M 41/48* (2013.01); *C12Q 1/02* (2013.01); *G01N 15/06* (2013.01); *G01N 21/47* (2013.01); *G01N 21/51* (2013.01); *G01N 21/53* (2013.01); *G01N 21/59* (2013.01); *G01N 2015/0053* (2013.01); *G01N 2015/0065* (2013.01); *G01N 2015/0693* (2013.01); *G01N 2201/12* (2013.01)

(56) References Cited

U.S. PATENT DOCUMENTS

2008/0317632 A1   12/2008   Shimasaki et al.
2011/0211058 A1   9/2011   McCollum et al.

FOREIGN PATENT DOCUMENTS

| | | |
|---|---|---|
| JP | 2008-79554 A | 4/2008 |
| JP | 4402249 B2 | 1/2010 |
| JP | 4775218 B2 | 9/2011 |
| WO | WO 2011/043731 A1 | 4/2011 |

OTHER PUBLICATIONS

Japanese-language Written Opinion (PCT/ISA/237) issued in PCT Application No. PCT/JP2015/069617 dated Oct. 13, 2015 (Four (4) pages).

* cited by examiner

[FIG. 1]
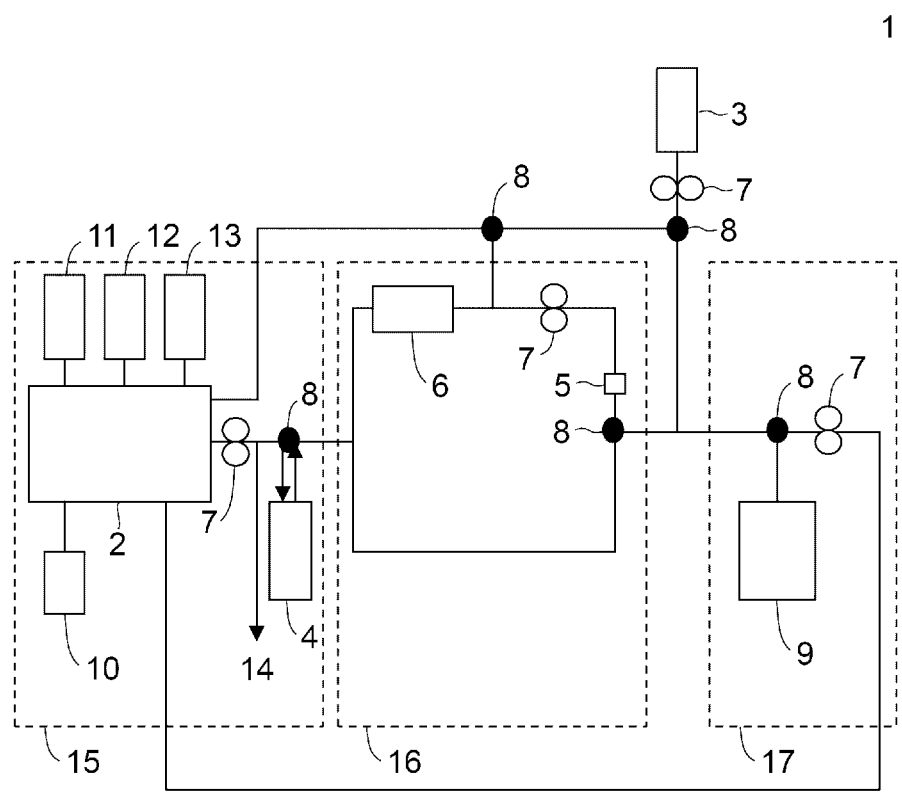
[FIG. 2]
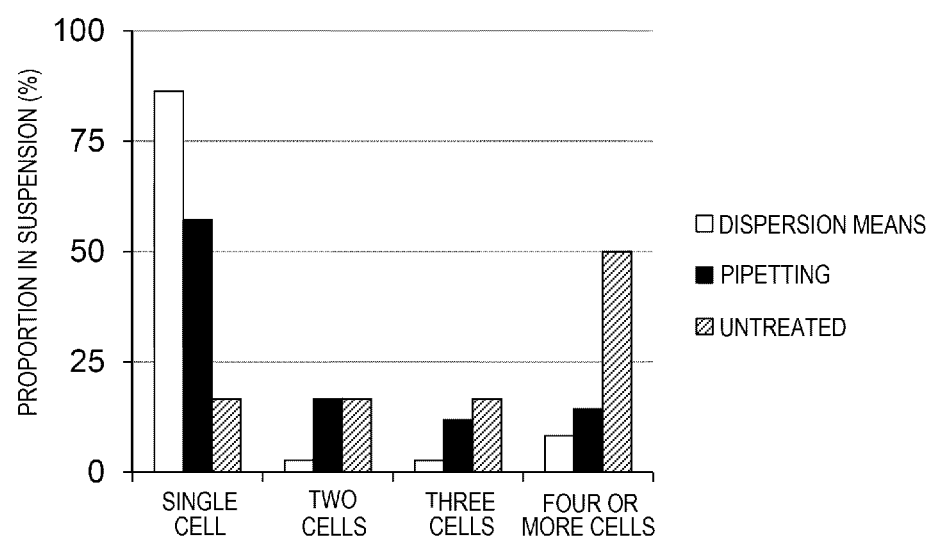

[FIG. 3]
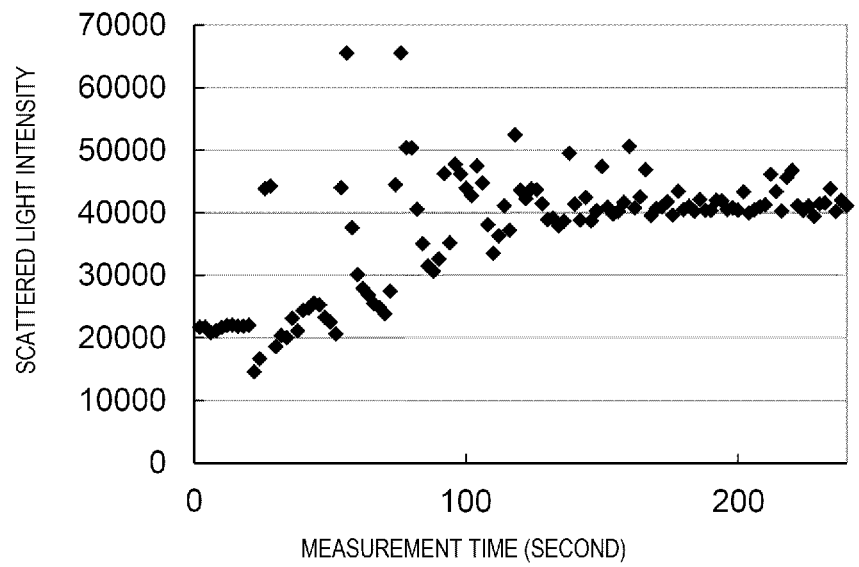
[FIG. 4]
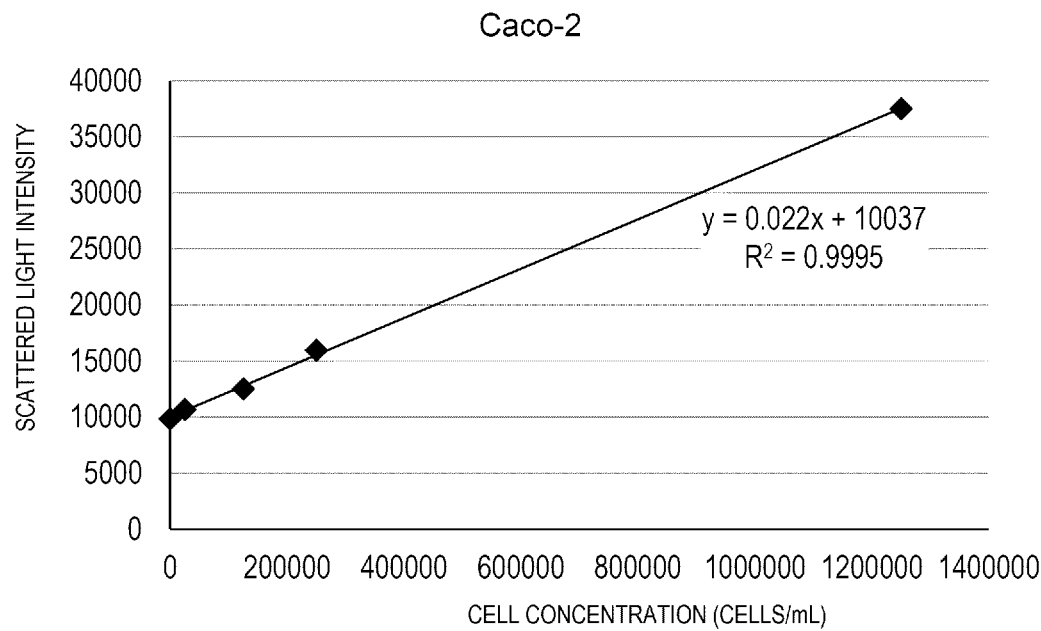

[FIG. 5]
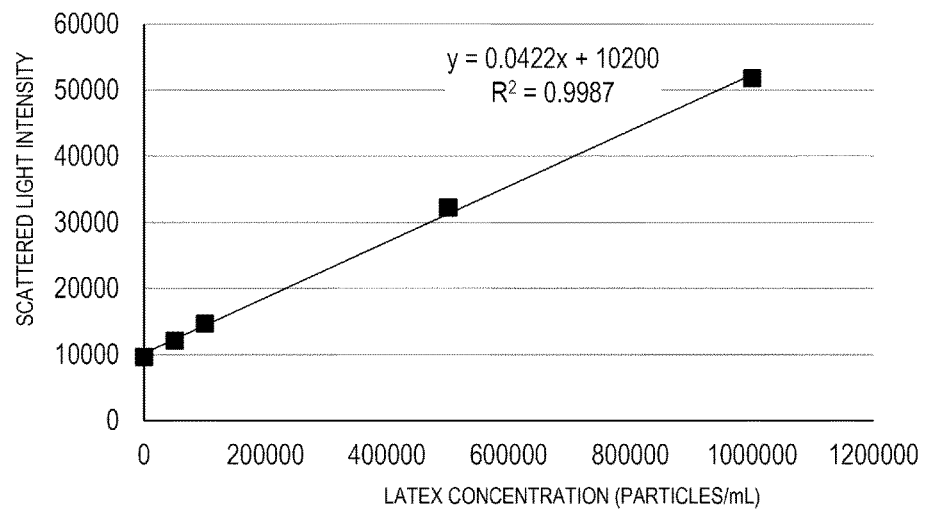
[FIG. 6]
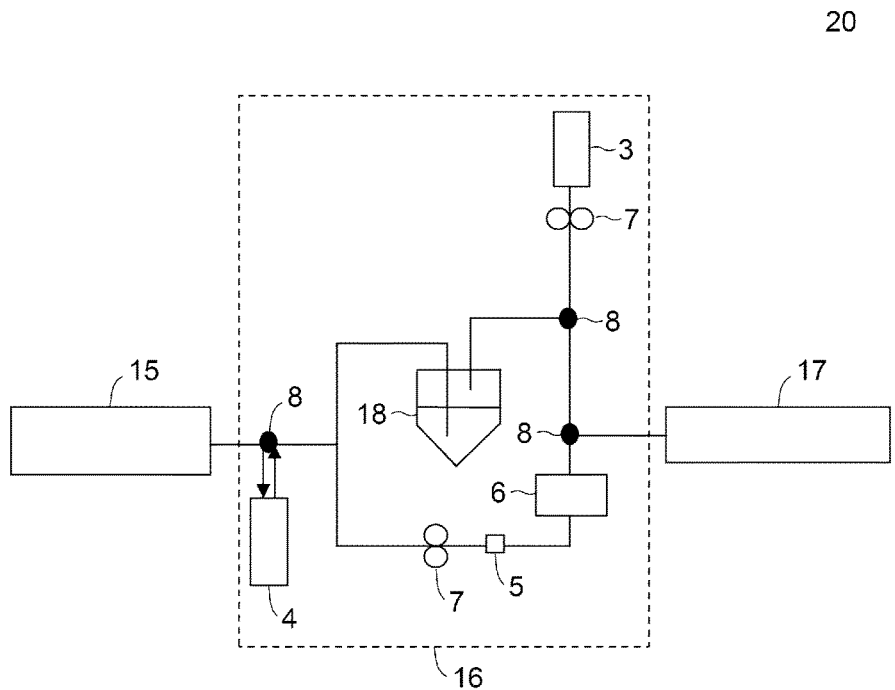

[FIG. 7]
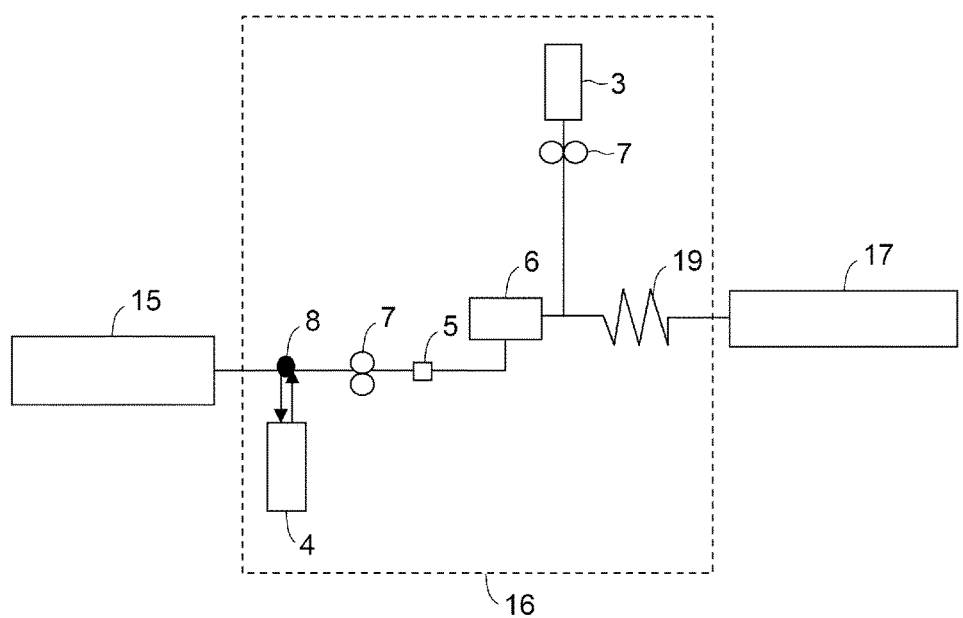

[FIG. 8]
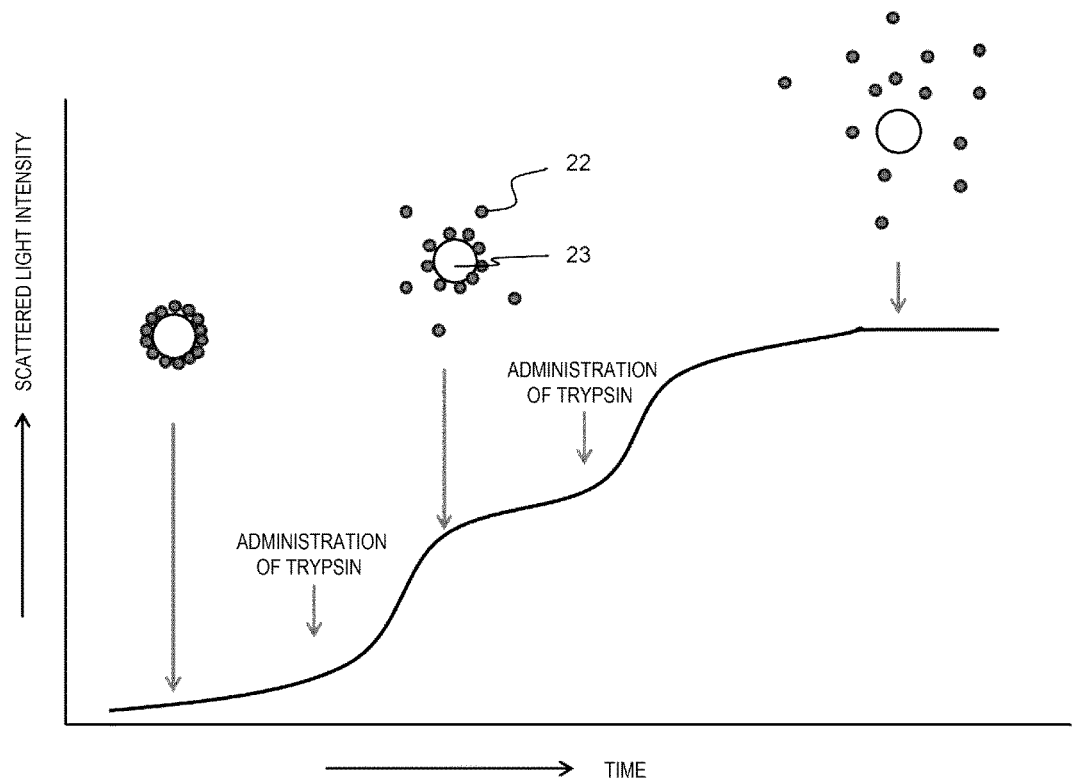
[FIG. 9]
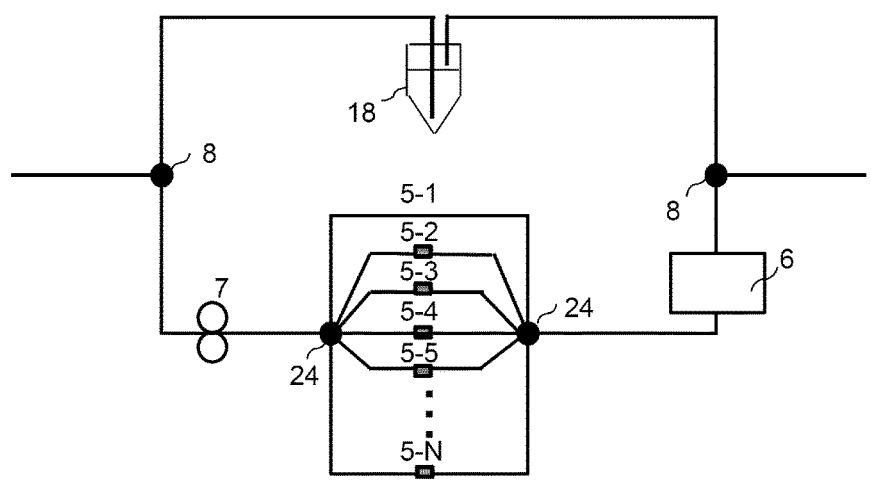

CELL DISPERSION MEASUREMENT MECHANISM, AND CELL SUBCULTURE SYSTEM UTILIZING SAME

TECHNICAL FIELD

The present invention relates to a cell dispersion measurement mechanism, an automated cell culture apparatus equipped with the cell dispersion measurement mechanism and a cell dispersion measurement method.

BACKGROUND ART

When anchorage-dependent cells are cultured, most of the operations have been conducted manually. However, because the cell culture operations are complex and take a long time, enormous labor costs are required. Also, the timings of the medium exchange and the subculture operation and the like are determined based on the experiences of each operator. As a result, the damage caused by the subculture operation to the cells varies with the operator, and the cell viability varies. Thus, a difference is apt to arise in the state of cells after the subculture operation.

Accordingly, as shown in PTLs 1 and 2, a method for determining the timings of the medium exchange operation and the subculture operation by calculating the number and concentration of cells and the like based on the image data of the cultured cells has been proposed. In general, cells which have been just detached from a culture container by the action of an enzyme or a polymer membrane or mechanical action are in the state of masses due to the intercellular adhesion and have to be separated by swaying the container or pipetting (cell dispersion operation). PTLs 1 and 2, however, do not clearly disclose the cell dispersion operation. Also, when the number of cells of a cell suspension in which the cells are not fully dispersed is calculated based on image data obtained from limited microscope fields, a major error is apt to arise in the estimated total number of cells.

PTL 3 describes a cell culture apparatus which can automate the recovery of cultured cells and which can subculture the cells efficiently. PTL 3 describes a cell dispersion step of removing the intercellular adhesion of cultured cell masses and dispersing the cultured cells in a collected fluid by causing the cultured cell masses detached from the walls of the culture container to flow through a thin tube attached to flowing means connected to the discharge port of the culture container. However, the cell culture apparatus described in PTL 3 does not have a mechanism for calculating the number and concentration of cells in the cell suspension obtained in the cell dispersion step. When a cell suspension whose number and concentration of cells are not measured accurately is used, a difference is apt to arise in the state of cells after the subculture operation.

CITATION LIST

Patent Literature

PTL 1: U.S. Pat. No. 4,402,249
PTL 2: US patent application publication No. 2011/0211058 A1
PTL 3: U.S. Pat. No. 4,775,218

SUMMARY OF INVENTION

Technical Problem

An object of the invention is to provide a cell dispersion measurement mechanism whereby it becomes possible to fully disperse cells regardless of the experiences of operators skilled in cell culture and it also becomes possible to determine the number or concentration of cells accurately, an automated cell culture apparatus equipped with the cell dispersion measurement mechanism and a cell dispersion measurement method.

Solution to Problem

As a result of extensive investigation to solve the problems, the present inventors have found that the number or concentration of cells contained in a cell suspension can be measured accurately by circulating the cell suspension in a flow path and then measuring over time the number or concentration of cells and/or the degree of dispersion of cells contained in the cell suspension that is flowing in the circulation flow path. The invention has been thus completed.

Accordingly, the invention includes the following embodiments.

1. A cell measurement apparatus including a flow path in which a cell suspension flows, liquid driving means which sends the cell suspension in the flow path and measurement means which measures over time the number or concentration of cells and/or the degree of dispersion of cells contained in the cell suspension flowing in the flow path while mixing the cell suspension using the liquid driving means.

2. A cell dispersion measurement mechanism having the cell measurement apparatus according to 1 above and dispersion means which disperses cell masses contained in the cell suspension.

3. The cell dispersion measurement mechanism according to 2 above, wherein the measurement means measures by a scattered light intensity or transmittance.

4. The cell dispersion measurement mechanism according to 2 or 3 above, wherein the dispersion means causes a shearing force in the cell suspension.

5. The cell dispersion measurement mechanism according to 4 above, wherein the shearing force is caused by a flow path having a reduced sectional area.

6. The cell dispersion measurement mechanism according to 5 above further having cell dispersion measurement mechanism control means which controls at least the liquid driving means based on data obtained with the cell measurement apparatus, wherein the control means determines whether or not the degree of dispersion of cells has reached a predetermined degree based on the data obtained with the cell measurement apparatus and drives the liquid driving means in such a manner that the cell suspension passes through the flow path having a reduced sectional area when the degree of dispersion has not reached the predetermined degree.

7. The cell dispersion measurement mechanism according to 6 above, wherein the flow path having a reduced sectional area is provided with a flow path-pressing device which presses a flow path made of an elastic material and which sets the degree of constriction of the flow path at any degree, and the control means controls the flow path-pressing device based on the data obtained with the cell measurement apparatus.

8. The cell dispersion measurement mechanism according to 6 above, wherein the flow path has at least two or more flow paths in parallel, the parallel flow paths are designed in such a manner that a part of the flow paths is selected with a switch valve to pass the cell suspension, and the flow path having a reduced sectional area is provided in at least one flow path included in the parallel flow paths.

9. The cell dispersion measurement mechanism according to 8 above having two or more flow paths having a reduced sectional area, wherein the sectional areas of the flow paths having a reduced sectional area are different.

10. An automated cell culture apparatus having an extended culture mechanism which cultures and grows cells and which detaches the grown cells, the cell dispersion measurement mechanism according to any one of 2 to 9 above which disperses and measures the cells detached by the extended culture mechanism and a cell seeding mechanism which sends the cell suspension in which the cells are dispersed by the cell dispersion measurement mechanism to the extended culture mechanism.

11. The automated cell culture apparatus according to 10 above including an automated cell culture apparatus control unit which stores the growth rate of the cells and adjusts the concentration of the cell suspension at a predetermined concentration determined based on the growth rate.

12. A cell dispersion measurement method including a step of circulating a cell suspension in a flow path, a step of dispersing cell masses contained in the cell suspension and a step of measuring over time the number or concentration of cells and/or the degree of dispersion of cells contained in the cell suspension flowing in the circulation flow path.

13. The cell dispersion measurement method according to 12 above, wherein the measurement in the measurement step is conducted by a scattered light intensity or transmittance.

14. The cell dispersion measurement method according to 12 or 13 above, wherein a shearing force is caused in the cell suspension in the dispersion step.

15. The cell dispersion measurement method according to 14 above, wherein the shearing force is caused by a flow path having a reduced sectional area.

This description includes the contents disclosed in Japanese patent application No. 2014-148768 to which this application claims priority.

Advantageous Effects of Invention

According to the mechanism and the method of the invention, a cell suspension is made uniform and measured. Thus, there is no variation caused by sampling, and accurate measurement of the number or concentration of cells becomes possible.

BRIEF DESCRIPTION OF DRAWINGS

FIG. 1 The first example of the structure of the automated cell culture apparatus in the invention is shown.

FIG. 2 The proportions of single cells and cell masses in a suspension which passed through the dispersion means (diameter of orifice of 0.7 mm×length of 1 mm) in an embodiment of the invention 10 times, in a suspension which was pipetted 10 times or in an untreated suspension are shown. Microphotographs were taken after each treatment, and the numbers of the single cells and the cell masses in the cell suspensions were counted by image processing.

FIG. 3 The change in the scattered light intensity of Caco-2 cells over time caused by the dispersion treatment of the invention is shown.

FIG. 4 The calibration curve of the concentration of Caco-2 cells and the scattered light intensity is shown.

FIG. 5 The calibration curve of the concentration of latex particles having a particle diameter of 10 μm and the scattered light intensity is shown.

FIG. 6 The second example of the structure of the automated cell culture apparatus in the invention is shown.

FIG. 7 The third example of the structure of the automated cell culture apparatus in the invention is shown.

FIG. 8 An example of the measurement of cells adhered to a culture support by the cell dispersion measurement mechanism of the invention is shown.

FIG. 9 An example of the cell dispersion mechanism in the invention is shown.

FIG. 10A shows the optimization of the inside diameter of the orifice; FIG. 10B shows the optimization of the passing period; FIG. 10C shows the optimization of the flow rate of the pump; and FIG. 10D shows the optimization of the length of the orifice. The optimum conditions are those under which the number of cell masses is the smallest.

DESCRIPTION OF EMBODIMENTS

Figure 10A:
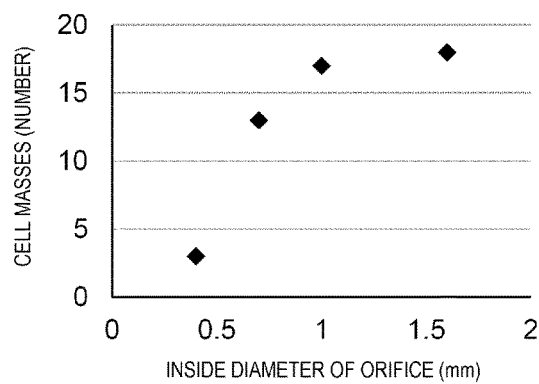
FIGS. 10A-10D The results of optimization of the conditions for dispersing cells using the cell dispersion mechanism of FIG. 9 are shown.

In an embodiment, the invention relates to a cell measurement apparatus including a flow path in which a cell suspension flows, liquid driving means which sends the cell suspension in the flow path and measurement means which measures over time the number or concentration of cells and/or the degree of dispersion of cells contained in the cell suspension flowing in the flow path while mixing the cell suspension using the liquid driving means.

In the invention, the shape of the flow path is not particularly limited. The flow path may be a circular flow path or a linear flow path which is explained below using FIG. 7.

In this description, the liquid driving means is not particularly limited. For example, a liquid may be sent by a stream of water caused in the flow path with rotation means such as a screw provided in the flow path, or a liquid may be sent by applying pressure from outside. Because the load applied to cells is light, in particular, it is preferable to drive a liquid by applying pressure from outside. An example of the liquid driving means which sends a liquid by applying pressure from outside is a Perista pump or the like which moves a fluid by squeezing the flow path from outside.

In this description, the "dispersion of cells" means that cell masses formed by intercellular adhesion are separated into individual cells. Also, the "degree of dispersion of cells" means the degree of dispersion of the cells contained in the cell suspension. The degree of dispersion becomes higher as the cell suspension contains less cell masses, while the degree of dispersion becomes lower as more cell masses are contained.

In the invention, the means and the method for dispersing the cells are not particularly limited. The cells may be dispersed by chemical means, for example proteases such as trypsin, collagenase and Dispase, and the cells may be dispersed by physical means, for example vortex mixing, pipetting and stirring. One or more thereof may be combined. In the invention, the cell masses contained in the cell suspension may be dispersed by sending or circulating the cell suspension, for example by a stream of water caused by sending or circulating the cell suspension, and liquid driving or circulation of the cell solution also plays the dispersing role in this case. Thus, in the cell dispersion measurement mechanism of the invention, liquid driving and dispersion may be achieved by same means. Similarly, in the cell dispersion measurement method of the invention, circulation of the cell suspension and dispersion of the cell masses may be achieved by a same step.

The invention also relates to a cell dispersion measurement mechanism having the cell measurement apparatus and dispersion means which disperses cell masses contained in the cell suspension. In the invention, the cells may be dispersed by causing a shearing force in the cell suspension, and the shearing force can be caused by a flow path having a reduced sectional area (also referred to as a "constricted part" in this description). In this case, a flow path having a partially narrow sectional area may be used, or the sectional area of a part of the flow path may be reduced by providing a division plate such as an orifice. The flow path having a reduced sectional area may have a sectional area for example 1.1 to 100 times, 2 times to 10 times, in particular 3 times to 5 times as small as the sectional area of the flow path. For example, when the inside diameter of the flow path is about 3 mm, the diameter of the reduced sectional area may be about 0.05 to 2 mm, about 0.1 mm to 1 mm, in particular about 0.5 to 0.8 mm. The diameter of the reduced sectional area can be changed appropriately depending on the cell size, the adhesiveness and the like.

The degree of dispersion of the cells can be adjusted by various conditions. For example, when a constricted part is used as the dispersion means, the degree of dispersion can be adjusted by the number of constricted parts, the inside diameter of the constricted part, the length of the constricted part, the number of times the cells pass through the constricted part, the flow rate, the inside diameter of the flow path and the like.

The constricted part may be formed by a flow path-pressing device which can control the degree of pressing of the flow path instead of an orifice. The flow path-pressing device has a function of pressing an elastic flow path from outside and presses the flow path while keeping a certain space, rather than completely closing as a pinch valve. The flow path-pressing device is preferably controlled by a control unit. By changing the degree of pressing of the flow path, the shearing force applied to the cell aggregates in the cell suspension flowing inside can be changed. Also, in the case where the cell aggregates are still large, the flow path may be clogged with the cells when the sectional area of the constricted part of the flow path is too small. However, when the flow path-pressing device, which can change the degree of pressing of the flow path, is used, such a problem can be avoided by selecting an adequate degree of pressing of the flow path.

The control unit preferably controls the flow path-pressing device based on data on the degree of dispersion of cells obtained from the cell dispersion measurement mechanism and changes the degree of pressing of the flow path. For example, the flow path-pressing device may be able to change the space from the fully open state in which the flow path is not pressed at all to the closed state in which the flow path is completely pressed and control the size of the space using an actuator which can determine the position like a stepper motor. Alternatively, the space may be determined by inserting a member which serves as an indicator of the space size. Such a member may be able to correspond to more than one space size. In this regard, the flow path-pressing device may be employed instead of an orifice also in the dispersion means explained below using FIGS. 1, 6, 7 and 8.

In addition to the flow path-pressing device, it is also possible to provide two or more parallel flow paths having different dispersion means so that a flow path can be selected with a switch valve. In this manner, based on the data on the degree of dispersion of cells obtained from the cell measurement apparatus, the cell aggregates can be caused to pass through an orifice having a large diameter for example when the cell aggregates are determined to be relatively large, and the cell masses can be caused to pass through a smaller orifice when the cell masses are determined to have been separated to some extent. A flow path can be selected by controlling the switch valve with the control unit. With such a structure, appropriate cell dispersion treatment can be conducted based on the data on the degree of dispersion of cells obtained from the cell measurement apparatus without a complex structure like the flow path-pressing device, and the orifices can be prevented from being clogged with the cell masses.

In this description, the method for measuring the number or concentration of cells and/or the degree of dispersion of cells contained in the cell suspension is not particularly limited. For example, the number or concentration of cells and/or the degree of dispersion of cells may be measured from an image by providing an observation window in the flow path and taking an image with a microscope equipped with a CCD camera or may be measured by the scattered light intensity or the transmittance using a flow cell and a light source. Fluorescence may also be used for the measurement. When the number or concentration of cells is measured based on the scattered light intensity or the transmittance, the scattered light intensity becomes higher and the transmittance becomes lower as the number or concentration of cells becomes higher. Also, when the degree of dispersion of cells is measured based on the scattered light intensity or the transmittance, the variation in the measured value becomes smaller and the change in the measured value with the dispersion process becomes smaller as the degree of dispersion of cells becomes higher. The measurement by the scattered light intensity or the transmittance is preferable because the measurement allows rapid treatment, results in better dynamic range and reproducibility in measuring cells than in cell measurement based on image data obtained from limited microscope fields and allows accurate measurement of the number or concentration of cells and/or the degree of dispersion of cells.

In the invention, the quantitative determination of the cell suspension is not particularly limited but can be conducted for example by the same method as the quantitative determination of the colorimetric analysis of a solution. That is, the scattered light intensities or the transmittance of several kinds of sample having known concentrations are measured in advance using the same cells or beads having the same particle diameter, and a calibration curve is created. Using this calibration curve, the concentration of cells can be calculated by substituting the scattered light intensity or the transmittance obtained from the cell suspension having an unknown concentration into the correlating equation.

In an embodiment, the cell dispersion measurement mechanism of the invention measures over time the number or concentration of cells and/or the degree of dispersion of cells contained in the cell suspension. In this description, "to measure over time" means to measure with the passage of time. The measurement over time may be continuous measurement or discontinuous measurement at a measurement interval. The measurement interval in the discontinuous measurement is not particularly limited but may be for example 0.01 seconds to 50 seconds, 0.1 seconds to 5 seconds, in particular one second to two seconds.

In an embodiment, the invention relates to an automated cell culture apparatus having an extended culture mechanism which cultures and grows cells and which detaches the grown cells, a cell dispersion measurement mechanism which disperses and measures the cells detached by the extended culture mechanism and a cell seeding mechanism which sends a cell suspension in which the cells are dispersed by the cell dispersion measurement mechanism to the extended culture mechanism. In an embodiment, the automated cell culture apparatus includes an automated cell culture apparatus control unit which stores the growth rate of the cells and adjusts the concentration of the cell suspension at a predetermined concentration determined based on the growth rate.

In this description, the "growth rate of the cells" means the rate at which the cells increase and decrease in number with the passage of time. The growth rate can be represented for example by a growth curve of the cells. In this description, the "predetermined concentration" means the concentration of the cells which can grow to a desired number of cells after being cultured for a certain period. For example, when a plate containing cells which will be at 50% confluence in a culture container having a base area of 78.5 cm$^2$ in two days is required, the concentration of the cell suspension from which the cells grow to the cell number in the culture container in two days is the "predetermined concentration". The predetermined concentration can be determined for example from a growth curve of the cells.

In the invention, "to adjust at a predetermined concentration" means for example to dilute the cell suspension to the predetermined concentration with a diluent such as physiological saline, a culture medium and PBS when the concentration of the cell suspension is higher than the predetermined concentration, and the term means not to dilute or to concentrate the cell suspension to the predetermined concentration when the concentration of the cell suspension is the predetermined concentration or lower. In the apparatus and the method according to the invention, the concentration of the cell suspension is measured accurately. Thus, using the prediction function based on the growth rate, a desired number of cells can be obtained accurately at a desired time on a desired day in subculturing.

In this description, the extended culture mechanism may have one, two or more culture containers. When two or more culture containers are included, the culture containers may differ from each other in size, shape, material and the like. The culture container(s) is not particularly limited as long as cells are grown, but the culture container(s) may be for example a culture plate, a culture flask and the like. The cell seeding mechanism may send the cell suspension to a culture container which has been washed after use or send the cell suspension to a new cell culture container.

In the automated cell culture apparatus according to the invention, the cell suspension may be taken out of any of the extended culture mechanism, the cell dispersion measurement mechanism and the cell seeding mechanism and used for further culture or for an assay. The automated cell culture apparatus according to the invention may have an acquisition mechanism for taking the cell suspension out of any of the extended culture mechanism, the cell dispersion measurement mechanism and the cell seeding mechanism.

In an embodiment, the invention relates to a cell dispersion measurement method including a step of circulating a cell suspension in a flow path, a step of dispersing cell masses contained in the cell suspension and a step of measuring over time the number or concentration of cells and/or the degree of dispersion of cells contained in the cell suspension flowing in the circulation flow path. The cell dispersion measurement method may use the cell dispersion measurement mechanism according to the invention but does not have to use the cell dispersion measurement mechanism.

In the mechanism and the method of the invention, the process in which the cell masses in the cell suspension are dispersed from the state in which many cell masses are contained is monitored in real time. Thus, the dispersion operation can be controlled in such a manner that a necessary and sufficient degree of dispersion of cells can be obtained. As a result, the damage to the cells can be minimized, and the cell viability can be maintained at the maximum. Also, because the cells are fully dispersed in the cell suspension and maintained in a uniform state, the variation in subcultures caused by the precipitation of the cells during sending, a difference in the degree of dispersion or the like can be prevented.

Moreover, the automated cell culture apparatus of the invention can automate all the cell subculture operations and thus can reduce labor, and human errors caused by the difference in the levels of skill of the operators can be reduced.

The cell dispersion measurement mechanism, the cell culture apparatus equipped with the cell dispersion measurement mechanism and the cell dispersion measurement method according to the invention are explained below using the drawings, but the invention is not limited to these embodiments.

The first example of the structure of the automated cell culture apparatus according to the invention is shown schematically in FIG. 1. An automated cell culture apparatus 1 is composed of an extended culture mechanism 15 which cultures and grows cells and which detaches the grown cells, a cell dispersion measurement mechanism 16 which disperses and measures the cells detached by the extended culture mechanism, a cell seeding mechanism 17 which sends a cell suspension in which the cells are dispersed by the cell dispersion measurement mechanism to the extended culture mechanism and a control mechanism (not shown in the figure). The control mechanism (also referred to as "control unit" or "control means" in this description) may control the whole apparatus or may control the extended culture mechanism 15, the cell dispersion measurement mechanism 16 and the cell seeding mechanism 17 or one means or more of the mechanisms. An example of the control mechanism is a calculator (computer) having a program for controlling each means or mechanism.

In this description, the "cell dispersion measurement mechanism control means" indicates means which controls the cell dispersion measurement mechanism. For example, the cell dispersion measurement mechanism control means can determine the amount of a diluent necessary for adjusting the number or concentration of the cells at a desired concentration based on data obtained with the cell measurement apparatus, incorporate the necessary amount of the diluent into the flow path and drive the liquid driving means to mix the cell suspension and the diluent. Also, the cell dispersion measurement mechanism control means may determine whether or not the degree of dispersion of cells has reached a predetermined degree based on the data obtained with the cell measurement apparatus and drive the liquid driving means in such a manner that the cell suspension passes through the constricted part when the degree of dispersion has not reached the predetermined degree. In this description, the "automated cell culture apparatus control unit" means a unit which controls the automated cell culture apparatus. For example, the automated cell culture apparatus control unit controls a valve and/or a liquid driving unit provided in the flow path which connects the mechanisms to adjust the concentration of the cell suspension at a predetermined concentration based on the data obtained with the cell measurement apparatus.

The extended culture mechanism 15 is housed in a $CO_2$ incubator. The cell dispersion measurement mechanism 16 and the cell seeding mechanism 17 may also be housed in a $CO_2$ incubator. The whole flow path in the automated cell culture apparatus 1 is a closed system and is sterile, and the air supplied into the flow path during the operation is supplied through a HEPA filter. Thus, cell culturing including the cell passage operation can be conducted in a sterile environment.

The cells cultured in an extended culture container 2 are supplied from cell supply means 10 using a syringe pump or the like which is liquid driving means. Then, an adequate amount of a culture medium is supplied by culture medium supply means 3. After swaying the container with an automatic driving system so that the concentration of the cells becomes uniform in the culture medium, the container is left still, and the cells are cultured in a $CO_2$ incubator under adequate conditions (for example 37° C., $CO_2$ concentration of 5%) for several days. During the period, the bottom area occupancy of the cells in the extended culture container 2 is observed with a microscope, and the cells are grown to the state in which the cell growth rate does not decrease (before 100% confluence). Then, the culture medium, dead cells, waste and the like are removed using a suitable washing solution for the cells, such as PBS (Phosphate Buffered Saline) or HEPES (4-(2-hydroxyethyl)-1-piperazineethanesulfonic acid) buffer, which is supplied from cell washing solution supply means 11. Next, a protease such as trypsin, collagenase and Dispase is supplied from cell detachment solution supply means 12, and the mixture is left at 37° C. for a certain period. A protein such as integrin which adheres the cells to the bottom surface of the culture container is degraded by the enzyme, and the cells are detached from the extended culture container 2. Because the enzyme does not completely degrade a protein which adheres the cells, there are many masses of cells after detaching the cells. Also, the activity of the cells becomes weak when the cells are left in the presence of the enzyme for a long time, and the growth after seeding deteriorates or dead cells increase in number. Thus, it is necessary to determine the optimum conditions for the detachment. When the conditions are stored in the automated cell culture apparatus control unit, the optimum cell detachment operation can be conducted automatically. After detaching the cells, an enzyme activity inhibitor such as a trypsin inhibitor or the culture medium is supplied from cell detachment solution inhibitor supply means 13 to stop the activity of the protease. As a result, the damage caused by the enzyme activity to the cells is reduced.

Next, a detached cell sample supplied from the extended culture container 2 is recovered and sent to sample introduction means 4. When the amount of the cell residue at the bottom of the extended culture container 2 is high, the recovery rate can be increased by washing the bottom surface of the container several times with the culture medium supplied from the culture medium supply means 3 and sending and recovering the resultant solution in the sample introduction means 4.

The recovered detached cell sample, preferably the total amount thereof, is supplied as a cell suspension into a circular pipe of the cell dispersion measurement mechanism 16 using a syringe pump or the like which is liquid driving means. Dispersion means 5, measurement means 6 and a Perista pump 7 which is liquid driving means are in the circular pipe which is a circulation flow path. Most of the cells contained in the cell suspension before being treated with the cell dispersion measurement mechanism 16 are in the state of masses of several dozen cells or of sheet-like masses. By passing the cell suspension through the dispersion means 5, a dispersing effect which is equivalent to or better than that of pipetting can be obtained. The conditions necessary for dispersing the cells vary with the cell size, the adhesiveness and the like, and the conditions for dispersing can be changed appropriately depending on the kind of the cells.

When the Perista pump 7 is operated, the sample circulates in the circular pipe, is dispersed every time the sample passes through the dispersion means 5 and is measured by the measurement means 6. The automated cell culture apparatus control unit stores the relation between the degree of dispersion of the cells used and the measured value in advance and controls the cell dispersion measurement mechanism and the cell seeding mechanism to send the cell suspension to cell seeding sample preparation means 9 by switching three-way valves 8 when it is determined from the results of monitoring of the change in the measured value of the cells over time that the cells are in the optimum state for seeding. The automated cell culture apparatus control unit calculates the concentration of the cell suspension from the value measured by the measurement means 6 based on the calibration curve which is stored in advance. Also, the automated cell culture apparatus control unit calculates the number and concentration of cells for seeding which can grow to a desired cell number after a certain period based on the growth curve which is stored in advance, and the automated cell culture apparatus control unit controls the cell dispersion measurement mechanism and the cell seeding mechanism to supply the culture medium necessary for diluting the cell suspension to the concentration from the culture medium supply means 3, send the culture medium to the cell seeding sample preparation means 9 and mix with the cell suspension. In the cell seeding sample preparation means 9, the culture medium and the cell suspension may be mixed by circulating in the provided circulation pipe or mixed using a stirrer bar or the like provided in the container. When the cell seeding sample has become uniform, the cell seeding sample is sent by operating the Perista pump 7 and injected into the extended culture container 2.

The cell suspension may be diluted in the cell seeding sample preparation means 9 as described above but may also be diluted in the cell dispersion measurement mechanism 16. In this case, the diluent may be sent into the flow path of the cell dispersion measurement mechanism 16 from the culture medium supply means 3 as in FIG. 1, or a diluent bag, a switch valve and the like may be provided in a part of the flow path to send the diluent into the flow path. When the cell suspension is diluted in the cell dispersion measurement mechanism, the number of diluted cells can be measured more accurately. The cell suspension and the diluent may be each incorporated once or may be incorporated more than once in small divided portions. It is preferable to incorporate the cell suspension and the diluent in more than one portion, because the two solutions are mixed more easily and because the load applied to the cells can be reduced. At this point, mixing of the diluent becomes easy when a sample reservoir 18 which is explained below using FIG. 6 is provided.

After supplying the solutions to the extended culture container 2, the cells and the solutions are supplied to the bottom surface of the container equally and uniformly by constantly swaying the container with the automatic driving system. The cells injected into the extended culture container 2 can be cultured in the above manner and subjected to the passage operation again.

The second example of the structure of the automated cell culture apparatus of the invention is shown in FIG. 6. The automated cell culture apparatus 20 shown in FIG. 6 has the sample reservoir 18 added in the circular pipe of the cell dispersion measurement mechanism 16 in FIG. 1. When this flow path is used, it is not necessary to change the volume of the circular tube also when the volume of the sample cell suspension increases or decreases, and the concentration of the cell suspension sample after preparing the seeding sample can be measured at the same time.

The third example of the structure of the automated cell culture apparatus of the invention is shown in FIG. 7. In the linear flow path of the automated cell culture apparatus 21 shown in FIG. 7, the cells in the cell suspension are dispersed by moving the cell suspension back and forth several times through the dispersion means 5, rather than dispersing and measuring the cells while circulating the sample as shown in FIG. 1. Moreover, rather than conducting the dispersion and the measurement of the cells at the same time, the cells are measured by the measurement means 6 to calculate the concentration of the cells after dispersion treatment of the cells, and the culture medium is supplied from the culture medium supply means 3 to adjust the concentration of the cells at the concentration for seeding. In the automated cell culture apparatus 21, the sample is caused to pass through a stirring coil 19 to mix the sample.

The dispersion of cells cultured using a support such as beads can be also measured by the cell dispersion measurement mechanism of the invention. FIG. 8 shows an example of the measurement of cells cultured using a support by the cell dispersion mechanism according to the invention. 22 shows the cell; 23 shows the culture support; the vertical axis shows the scattered light intensity; and the horizontal axis shows the time. FIG. 8 shows that the process in which cells cultured using a support are separated from the support by trypsin treatment into single cells can be monitored by the change in the scattered light intensity.

EXAMPLES

Example 1: Culture and Passage of Caco-2 Cells Using Automated Cell Culture Apparatus 1

First, the operations in the extended culture mechanism are explained. That is, $4.6 \times 10^6$ cells of Caco-2 (a human colon cancer cell line) which had been cryopreserved at −80° C. were suspended in 9 mL of a culture medium for Caco-2 (Minimum Essential Medium Eagle, Non-Essential Amino Acid Solution, 100 unit/mL Stabilized Penicillin, 100 μg/mL Streptomycin and 0.25 μg/mL Amphotericin B) containing 10% FBS (Fetal Bovine Serum) and put into the cell supply means 10. A syringe pump was operated, and the total volume of the cells was seeded in the extended culture container 2 having a base area of 78.5 cm². After two days, according to observation with an inverted microscope, the cells were at 80% confluence, and thus the cell detachment operation was conducted. Specifically, an automatic operation was conducted as follows in the extended culture container 2. After removing the culture medium in the extended culture container 2 by letting the culture medium flow into the liquid waste using the Perista pump 7, 3 mL of PBS was supplied from the cell washing solution supply means 11 and distributed to the entire bottom surface by swaying the extended culture container 2, and the cells were thus washed. After removing PBS by suction with the Perista pump 7, 2 mL of 0.25% trypsin-1 mM EDTA was supplied from the cell detachment solution supply means 12 and distributed to the entire bottom surface by swaying the extended culture container 2, and the cells were left still at 37° C. for four minutes and detached. After confirming that there were no cells adhered to the bottom surface of the extended culture container 2 using an inverted microscope, 3 mL of the culture medium was supplied from the culture medium supply means 3 to stop the activity of trypsin, and the culture medium with the detached cells was sent to the sample introduction means 4 by operating the Perista pump 7.

Next, the operations in the cell dispersion measurement mechanism are explained. In this mechanism, the dispersion means 5, the measurement means 6, the Perista pump 7 and the three-way valve 8 are connected with a silicone tube having an inside diameter of 3.15 mm in the total length of 520 mm. A flow cell having a volume of 1 mL is in the measurement means and is connected to the flow path. First, the culture medium is supplied from the culture medium supply means 3, and the circular flow path is filled with the culture medium. When the culture medium is supplied at this point, the tube stopper of the Perista pump 7 is removed, and the three-way valve 8 in the circular flow path is switched so that no air bubbles enter the flow path. Next, the total volume (5 mL) of the cell suspension sample stored in the sample introduction means 4 is supplied to the circular flow path. The culture medium which is pushed out at this point flows into the cell seeding sample preparation means 9. When the stopper of the Perista pump 7 in the circular pipe is returned to the original position and the pump is operated, the supplied cell suspension sample is circulated in the circular flow path while passing through the dispersion means 5 and the measurement means 6.

The proportions of cell masses and single cells in a cell suspension which passed through the dispersion means 5 (diameter of orifice of 0.7 mm×length of 1 mm) in an embodiment of the invention 10 times, in a cell suspension which was pipetted 10 times or in an untreated cell suspension are shown in FIG. 2. Microphotographs were taken after each treatment, and the numbers of the cell masses or the single cells in the cell suspensions were counted by image processing, and the proportions of the single cells and the cell masses containing two to four cells were summarized in a bar graph. As a result, it was found that a dispersing effect which was equivalent to or better than that of manual pipetting was obtained by the dispersion method of the invention.

Simultaneously with the cell dispersion, the scattered light intensity (wavelength of 700 nm, measurement angle of 20 degrees) was measured by the measurement means 6. The change in the scattered light intensity of Caco-2 cells over time is shown in FIG. 3. The process in which the scattered light intensity changed as the cells in the cell suspension were circulated and dispersed over time was measured. That is, the measured scattered light intensities of the cell suspension varied widely in the beginning. However, each time the cell suspension passed through the dispersion means 5, the variation in the measured scattered light intensities gradually became smaller, and the change in the measured values with the dispersion step also became smaller. In particular, after about 160 seconds elapsed after starting the measurement, the variation in the measured scattered light intensities and the change in the measured values with the dispersion step became very small. From the results, it is understood that the cells in the sample were dispersed about 160 seconds after starting the measurement and that the cells were dispersed uniformly. It is preferable that the optimum dispersion period by the dispersion means 5 can be determined in this manner because the decrease in the cell activity caused by over circulation can be prevented.

Next, the operations in the cell seeding mechanism are explained.

By the following assay, the concentration of cells in a cell suspension was determined. That is, a calibration curve was created by measuring the scattered light intensities of several kinds of Caco-2 cell solution having known concentrations. Then, a measured scattered light intensity was substituted into the correlating equation, and the concentration of cells in the cell suspension was calculated. As a result, the concentration of the cell suspension was $1.2 \times 10^6$ cells/mL. The calibration curve of Caco-2 cells is shown in FIG. 4.

The optimum cell concentration for seeding to obtain desired cells was calculated by the automated cell culture apparatus control unit, and a necessary amount of the culture medium was supplied from the culture medium supply means 3. That is, the cell concentration for seeding was calculated automatically using the growth curve of Caco-2 cells which had been input in advance in the automated cell culture apparatus control unit, supposing that two culture plates having abase area of 78.5 cm² containing cells at 50% confluence were required in two days, and 15 mL of the culture medium was supplied from the culture medium supply means 3. The culture medium and the Caco-2 cells in the cell seeding sample preparation means 9 were mixed, and 10 mL of the resultant mixture was seeded in each of two plates provided in the extended culture container 2. In this manner, the cell passage operation was conducted automatically.

To confirm the activity of the cells after the passage, the seeded cells were cultured for two days, and the growth rate and the viability were examined. As a result, the concentration of the cells after two days was $3.8 \times 10^6$ cells/mL, and the cell viability was 96 to 97% (n=4). The apparent cell occupancy was 50% confluence.

Example 2: Comparison of Measurement Methods Using Latex Particles

Using latex particles, the measurement method by scattered light intensity and the measurement method using a cell counter, which is generally widely used, were compared. The sample used was latex particles (manufactured by Polysciences, Inc., 10 µm, Lot No. 643763) having a known concentration ($5.0 \times 10^5$ particles/mL, 5 mL, the solvent was $H_2O$).

In the measurement by scattered light intensity, the sample was put into the sample introduction means 4, and the total volume, 5 mL, was supplied to the circular pipe of the cell dispersion measurement mechanism 16 according to an embodiment of the invention. After making the sample uniform by circulation, the Perista pump 7 was stopped, and the sample was measured by the stopped-flow method. The calibration curve of the 10-µm latex particles at 0 to $1.0 \times 10^6$ particles/mL is shown in FIG. 5. The same sample was measured six times by the stopped-flow method. As a result, the average concentration was $5.2 \times 10^5$ particles/mL, the standard deviation was $0.0097 \times 10^5$ particles/mL, and the relative standard deviation RSD was 0.19%.

In the measurement using a cell counter, trypan blue dye and the sample each in 10 µL were prepared and thoroughly mixed by pipetting, and the resultant solution was used as the sample. With respect to the measurement method, the sample was loaded at two points A and B on a specialized slide, and the concentrations were measured three times in succession at A and B. The averages of the three measurements were calculated, and the average of the values of A and B was also determined. The same measurement was conducted using six specialized slides. As a result, the average concentration was $4.6 \times 10^5$ particles/mL, the standard deviation was $0.3 \times 10^3$ particles/mL, and the relative standard deviation RSD was 7.3%.

As shown above, the accuracy was higher and the variation was smaller in the measurement by scattered light intensity than in the measurement using a cell counter.

Example 3: Optimization of Dispersing Conditions Using NIH/3T3 Cells

When cells are dispersed using a constricted part, the conditions for dispersing include the inside diameter of the flow path, the inside diameter of the constricted part, the number of constricted parts, the length of the constricted part, the flow rate, the number of times the cells pass through the constricted part (calculated from the flow rate and the operation period) and the like. An example of the method for optimizing the inside diameter and the length of the constricted part, the flow rate and the number of times the cells pass through the constricted part of these conditions is shown below.

FIG. 9 shows an example of the cell dispersion measurement mechanism according to the invention in which the flow path is circular and in which the dispersion means 5 in FIG. 6 are aligned in parallel. By switching multiway (N-way) valves 24, one dispersion means can be selected.

A solution obtained by recovering 3.0 to $4.0 \times 10^6$ cells of undispersed NIH/3T3 cells with 20 mL of a medium was put into the sample reservoir 18 and circulated by operating the Perista pump 7, and automatic optimization was conducted by the following procedures.

First, the inside diameter and the length of the constricted part were optimized. The dispersion means 5-1 was without a constricted part and was composed of a flow path of 3.15 mm i.d.×720 mm as a whole. Constricted parts (orifices or the like) having the following sizes were provided in the dispersion means 5-2 to 5-7: 1.6 mm i.d.×1 mm (5-2), 1.0 mm i.d.×1 mm (5-3), 0.7 mm i.d.×1 mm (5-4), 0.4 mm i.d.×1 mm (5-5), 0.4 mm i.d.×10 mm (5-6) and 0.4 mm i.d.×30 mm (5-7). The constricted parts were selected by switching the flow paths with the multiway valves 24.

The flow rate and the operation period of the pump are fixed, and the measurement means 6 measures the cell sample which has passed through the dispersion means 5-1 and sends the results to the control unit. The standard value has been set in the control unit in advance, and when dispersion is determined to be insufficient, the control unit switches the multiway valves 24 and passes a new sample through the next dispersion means 5-2. Similarly, the control unit determines the degree of dispersion of the cell sample which has passed through the dispersion means 5-2 and further passes the sample through 5-3, 5-4 and 5-5 in this order when the degree of dispersion is insufficient. This is continued until the results of the measurement means 6 clear the standard value. When the standard value is not cleared after any of the conditions, the dispersion means which is the closest to the standard value is used for determining the optimum values. As a result of these procedures, the optimum inside diameter×optimum length of the constricted part was 0.4 mm i.d.×30 mm.

Next, the flow rate was optimized. Under the conditions of a fixed constricted part and a fixed operation period of the pump, the Perista pump 7 was regulated, and the flow rate to send the cell sample was changed to 20 mL/min, 30 mL/min and 40 mL/min. The flow rate at which the degree of dispersion was the closest to the standard value was used as the optimum value. As a result, the optimum flow rate was 40 mL/min.

Next, the number of times the cells pass through the constricted part was optimized. Because the number of times the cells pass through the constricted part can be calculated from the flow rate and the operation period of the pump, the operation period of the pump was optimized. The constricted part and the flow rate were fixed, and the degrees of dispersion after the passing periods of 90 sec, 180 sec and 270 sec, which are in proportion to the number of times of passing, were evaluated. As a result, the optimum passing period was 180 sec.

Figure 10B:
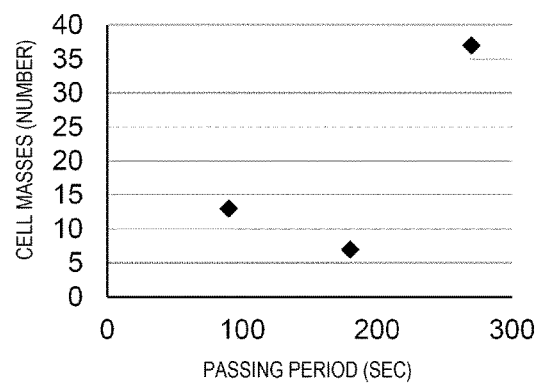
Figure 10C:
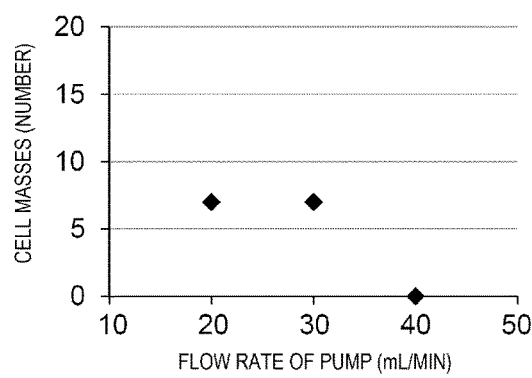
Figure 10D:
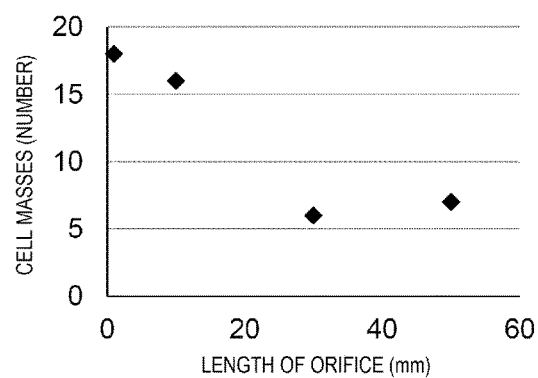

The above results are shown in FIG. 10. The value where the number of cell masses was zero was used as the standard value of the degree of dispersion. Also, when there was no constricted part, there were many cell masses, and thus the calculation was impossible.

When NIH/3T3 cells were dispersed under the optimized conditions for dispersing and subcultured, the viability after two days was 95% or more.

In this regard, when the degree of dispersion does not clear the standard value even when treatment under the optimized conditions for dispersing is conducted, the same sample may be treated again under different conditions for dispersing. In this case, it is preferable to change the conditions in the following order: 1) reduce the inside diameter of the dispersion means; 2) increase the flow rate of the Perista pump; and 3) increase the length of the dispersion means.

INDUSTRIAL APPLICABILITY

According to the invention, cells can be fully dispersed regardless of the experiences of operators skilled in cell culture, and the number or concentration of cells can be measured accurately.

REFERENCE SIGNS LIST

1: Automated cell culture apparatus 1
2: Extended culture container
3: Culture medium supply means
4: Sample introduction means
5: Dispersion means
6: Measurement means
7: Perista pump
8: Three-way valve
9: Cell seeding sample preparation means
10: Cell supply means
11: Cell washing solution supply means
12: Cell detachment solution supply means
13: Cell detachment solution inhibitor supply means
14: Liquid waste
15: Extended culture mechanism
16: Cell dispersion measurement mechanism
17: Cell seeding mechanism
18: Sample reservoir
19: Stirring coil
20: Automated cell culture apparatus 2
21: Automated cell culture apparatus 3
22: Cell
23: Culture support
24: Multiway (N-way) valve All of the publications, the patents and the patent applications cited in this description are incorporated in this description as they are by reference.

The invention claimed is:

1. A cell measurement apparatus comprising:
a flow path in which a cell suspension flows;
liquid driving means which sends the cell suspension in the flow path; and
measurement means which measures over time a number or concentration of cells and a degree of dispersion of cells contained in the cell suspension flowing in the flow path while mixing the cell suspension using the liquid driving means; and
dispersion means which disperses cell masses contained in the cell suspension;
wherein the measurement means measures a scattered light intensity or a transmittance of light from a light source; and
wherein the flow path is a circular flow path having a circular shape, in which the liquid driving means, the measurement means and the dispersion means are disposed.

2. The cell dispersion measurement mechanism according to claim 1, wherein the dispersion means causes a shearing force in the cell suspension.

3. The cell dispersion measurement mechanism according to claim 2, wherein the shearing force is caused by a flow path having a reduced sectional area.

4. The cell dispersion measurement mechanism according to claim 3, further comprising:
a cell dispersion measurement mechanism control means which controls at least the liquid driving means based on data obtained with the cell measurement apparatus, wherein the control means determines whether or not the degree of dispersion of cells has reached a predetermined degree based on the data obtained with the cell measurement apparatus and drives the liquid driving means in such a manner that the cell suspension passes through the flow path having a reduced sectional area when the degree of dispersion has not reached the predetermined degree.

5. The cell dispersion measurement mechanism according to claim 4, wherein the flow path having a reduced sectional area is provided with a flow path-pressing device which presses a flow path made of an elastic material and which sets the degree of constriction of the flow path at any degree, and the control means controls the flow path-pressing device based on the data obtained with the cell measurement apparatus.

6. The cell dispersion measurement mechanism according to claim 4, wherein the flow path has at least two or more flow paths in parallel, the parallel flow paths are designed in such a manner that a part of the flow paths is selected with a switch valve to pass the cell suspension, and the flow path having a reduced sectional area is provided in at least one flow path included in the parallel flow paths.

7. The cell dispersion measurement mechanism according to claim 6, further comprising:
two or more flow paths having a reduced sectional area, wherein sectional areas of the two or more flow paths having a reduced sectional area are different.

8. An automated cell culture apparatus having:
an extended culture mechanism which cultures and grows cells and which detaches the grown cells;
the cell dispersion measurement mechanism according to claim 1 which disperses and measures the cells detached by the extended culture mechanism; and a cell seeding mechanism which sends the cell suspension in which the cells are dispersed by the cell dispersion measurement mechanism to the extended culture mechanism.

9. The automated cell culture apparatus according to claim 8, further comprising:
an automated cell culture apparatus control unit which stores the growth rate of the cells and adjusts the concentration of the cell suspension at a predetermined concentration determined based on the growth rate.

10. The cell dispersion measurement mechanism according to claim 1, wherein the liquid driving means, the dispersion means, and the measurement means are disposed in the circular flow path.

11. The cell dispersion measurement mechanism according to claim 10, further comprising:
a three-way valve disposed in the circular flow path.

12. A cell dispersion measurement method including:
a step of circulating, by a liquid driving means, a cell suspension in a circular flow path;
a step of dispersing, by a dispersion means, cell masses contained in the cell suspension; and
a step of measuring, by a measuring means, over time a number or concentration of cells and a degree of dispersion of cells contained in the cell suspension flowing in the circulation flow path;
wherein the measurement in the measurement step is conducted by measuring a scattered light intensity or a transmittance of a light source; and
wherein the circular flow path has a circular shape, in which the liquid driving means, the measurement means and the dispersion means are disposed.

13. The cell dispersion measurement method according to claim 12, wherein a shearing force is caused in the cell suspension in the dispersion step.

14. The cell dispersion measurement method according to claim 13, wherein the shearing force is caused by a flow path having a reduced sectional area.

\* \* \* \* \*